United States Patent [19]

Umemura et al.

[11] 4,234,740

[45] Nov. 18, 1980

[54] PROCESS FOR PREPARING DIESTERS OF DICARBOXYLIC ACIDS

[75] Inventors: Sumio Umemura; Kanenobu Matsui; Yoshinari Ikeda; Katsuro Masunaga; Takumi Kadota, all of Ube, Japan

[73] Assignee: Ube Industries, Ltd., Ube, Japan

[21] Appl. No.: 964,363

[22] Filed: Nov. 28, 1978

[30] Foreign Application Priority Data

Dec. 9, 1977 [JP] Japan .................................. 52-147201

[51] Int. Cl.³ .............................................. C07C 67/38
[52] U.S. Cl. ....................................... 560/81; 560/114; 560/139; 560/146; 560/193; 560/198; 560/204
[58] Field of Search ................. 560/204, 81, 114, 146, 560/139, 193, 198

[56] References Cited

U.S. PATENT DOCUMENTS

| 3,397,226 | 8/1968 | Fenton .................................. 560/204 |
| 3,755,421 | 8/1973 | Fenton et al. ........................ 560/204 |
| 4,138,580 | 2/1979 | Umemura et al. ................... 560/204 |
| 4,138,587 | 2/1979 | Yamasaki et al. ................... 560/204 |

FOREIGN PATENT DOCUMENTS

| 42-13847 | 8/1967 | Japan ...................................... 560/204 |
| 43-9044 | 4/1968 | Japan ...................................... 560/204 |

*Primary Examiner*—Jane S. Myers
*Attorney, Agent, or Firm*—Frishauf, Holtz, Goodman & Woodward

[57] ABSTRACT

A process for preparing a diester of a dicarboxylic acid having two more carbon atoms than the unsaturated hydrocarbon used as the starting material, which comprises subjecting an unsaturated hydrocarbon, carbon monoxide and an alcohol to reaction in the presence of a platinum group metal or a salt thereof; a compound selected from the group consisting of nitric acid, a nitrogen oxide and an ester of nitrous acid; and a halogen compound.

16 Claims, No Drawings

PROCESS FOR PREPARING DIESTERS OF DICARBOXYLIC ACIDS

This invention relates to a novel process for preparing diesters of dicarboxylic acids.

More particularly, this invention relates to a process for preparing a diester of a dicarboxylic acid corresponding to the unsaturated hydrocarbon used as a starting material, namely a diester of a dicarboxylic acid having two more carbon atoms than the unsaturated hydrocarbon used, which comprises subjecting an unsaturated hydrocarbon, carbon monoxide and an alcohol to reaction in the presence of a platinum group metal or a salt thereof; a compound selected from the group consisting of nitric acid, a nitrogen oxide and an ester of nitrous acid; and a halogen compound, introducing molecular oxygen into the reaction system as occasion demands.

According to this invention, a diester of succinic acid is obtained when ethylene is used as the unsaturated hydrocarbon, and diesters of dicarboxylic acids such as succinic acid having substituent(s), e.g., alkyl, etc., and maleic acid are obtained as the diester of a dicarboxylic acid when an unsaturated hydrocarbon other than ethylene is used as the starting material. For example, when propylene is used as the unsaturated hydrocarbon, a diester of methylsuccinic acid is obtained; and when acetylene is used, a diester of maleic acid is obtained.

A process for preparing a diester of a dicarboxylic acid having two carbon atoms more than the unsaturated hydrocarbon used as the starting material, which comprises subjecting an unsaturated hydrocarbon, carbon monoxide and an alcohol to reaction, and introducing molecular oxygen into the reaction system as occasion demands is now widely known and various catalysts have been proposed for the reaction.

For example, U.S. Pat. No. 3,397,226 discloses an invention which employs as a catalyst a salt of a platinum group metal and a redox agent comprising a salt of a multivalent metal such as copper, iron, etc. However, it is taught that the reaction system should necessarily be kept substantially anhydrous by using a dehydrating agent such as isocyanates, diimides, orthoalkyl esters, etc., because this catalyst system brings about a decrease in the yield of the desired product, diester of dicarboxylic acid, due to water produced during the reaction and increased by-products such as carbon dioxide. Not only are the procedure and the control for maintaining an anhydrous reaction system very difficult and complicated according to this process but also the dehydrating agent used can not be re-utilized, since it is converted into an entirely different compound during the dehydration reaction. Accordingly, the cost for preparing a diester of a dicarboxylic acid becomes extremely high according to this conventional process.

A catalyst system in which an amino acid, a nickel compound and a metallic transition metal belonging to Group II, VII or VIII of the Periodic Table or the like are used in combination as the third substance instead of a dehydrating agent has also been proposed for improvement of conventional catalyst systems. Although the water-resistance of these catalyst systems is enhanced, the yield and the selectivity of the desired product have not necessarily been increased to a satisfactory extent. Further, the conventional catalyst systems generally have problems, e.g. the procedures of separation, recovery, regeneration, etc., of the product are complicated and the catalysts are expensive.

In view of these circumstances, the present inventors have made various studies eagerly to find out an industrially superior catalyst system to those proposed conventionally, which is to be used in the process for preparing a diester of a dicarboxylic acid corresponding to the unsaturated hydrocarbon used as the starting material, which comprises subjecting an unsaturated hydrocarbon, carbon monoxide and an alcohol to reaction, with introduction of molecular oxygen as occasion demands. As a result of the studies, the present inventors found that various defects of conventionally known catalyst systems can all be improved and a diester of a dicarboxylic acid can be prepared industrially with higher yield and higher selectivity, if a platinum group metal or a salt thereof; a compound selected from nitric acid, a nitrogen oxide and an ester of nitrous acid; and a halogen compound coexist within the reaction system; and thus accomplished this invention.

Namely, this invention relates to an industrially excellent process for preparing a diester of a dicarboxylic acid having two carbon atoms more than the unsaturated hydrocarbon used, which comprises subjecting an unsaturated hydrocarbon, carbon monoxide and an alcohol in the presence of (a) a platinum group metal or a salt thereof; (b) a compound selected from the group consisting of nitric acid, a nitrogen oxide and an ester of nitrous acid; and (c) a halogen compound, introducing molecular oxygen into the reaction system as occasion demands.

According to this invention, not only the yield and the selectivity of the desired diester of a dicarboxylic acid are increased in comparison with those of hitherto known processes but also expensive dehydrating agents and complicated procedures and controls for keeping the reaction system anhydrous are unnecessary since the decrease of catalytic activity due to the water formed during the reaction is not observed.

Further, the catalyst system of this invention is simple, being composed of a platinum group metal or salt thereof; nitric acid, a nitrogen oxide or an ester of nitrous acid; and a halogen compound. So, the procedures in separation, recovery and regeneration of the catalyst from the reaction system, and in the separation and obtaining of the desired product are simplified. Thus, the present process has various industrially superior merits to hitherto known processes and is extremely significant industrially.

The present invention will be explained further in detail as follows.

As the unsaturated hydrocarbons used in this invention, aliphatic and alicyclic hydrocarbons having 2 to 20 carbon atoms such as ethylene, propylene, butene, pentene, hexene, heptene, octene, nonene, decene, undecene, dodecene, tridecene, tetradecene, pentadecene, hexadecene, heptadecene, octadecene, nonadecene, eicosene and their isomers, and cyclopentene, cyclohexene, cycloheptene, cyclooctene, indene, styrene, allene, methylallene, butadiene, pentadiene, hexadiene, cyclopentadiene, etc.; and acetylene or alkyl derivatives thereof are useful.

As the alcohols employed may be mentioned mono- or dialcohols of alkyl cycloalkyl and aralkyl. Particularly, aliphatic alcohols such as methanol, ethanol, propanol, butanol, pentanol, hexanol, heptanol, octanol, nonanol, decanol, ethylene glycol, propylene glycol, butane diol, etc. are preferred and besides, cyclic alcohols such as cyclopentanol, cyclohexanol, cycloheptanol, phenol, naphthol, cresol, cumenol, xylenol, benzyl alcohol, phenyl ethanol, etc. are useful.

As the platinum group metal used as the catalyst, palladium is the most effective one and besides, platinum, rhodium, ruthenium, iridium, osmium, etc., are useful.

These platinum group metals may also be used in the form of a salt such as halide, nitrate, acetate, sulfate, phosphate and the like. When a halide of a platinum group metal is used, the halogen compound as mentioned below need not necessarily be used in combination.

In applying this invention industrially, it is convenient to use these platinum group metals or the salts thereof in the form of supported catalyst on such carriers as activated carbon, graphite, silica gel, alumina, silica alumina, diatomaceous earth, magnesia, pumice, molecular sieve, etc., in order to recover the platinum group metals or the salts thereof, or the desired product readily and to prevent the loss thereof.

These platinum group metals or the salts thereof are used in an amount of from 0.00001 to 10% by weight, preferably from 0.0001 to 1.0% by weight calculated on the platinum group metal against the reaction medium.

It is effective to use nitric acid, a nitrogen oxide or an ester of nitrous acid in an amount of from 0.0001 to 10 1 mole, preferably from 0.001 to 1 mole per liter of the reaction medium.

As the nitrogen oxide, nitrogen dioxide is the most effective but also useful is a nitrogen oxide such as dinitrogen trioxide, dinitrogen tetroxide, dinitrogen pentoxide, etc.

As the esters of nitrous acid used in this invention, all of the esters of nitrous acid with the above-mentioned alcohols used as a starting material in this invention are useful but preferred industrially are such esters as, in particular, methyl nitrite, ethyl nitrite, propyl nitrite, butyl nitrite, pentyl nitrite, hexyl nitrite and heptyl nitrite. An ester of nitrous acid which is gaseous at room temperature, e.g., methyl nitrite, ethyl nitrite, etc., may effectively be used in the form of its solution in a corresponding alcohol.

Further any halogen compound can be utilized in this invention if it contains a halogen atom therein. As the halogen compounds according to this invention, there may be exemplified a hydrogen halide; a halide of a platinum group metal such as palladium, platinum, rhodium, iridium, etc.; a halide of an alkali metal such as sodium, potassium, lithium, etc.; a halide of an alkaline earth metal such as calcium, magnesium, barium, etc.; a halide of a metal or nonmetal such as cobalt, zinc, nickel, copper, iron, chromium, antimony, tin, manganese, etc.; ammonium chloride; and so on. These halogen compounds may also be used after supported on a carrier for the platinum group metal mentioned above. The halogen compound may preferably be used in such an amount that the atomic ratio of the halogen to the platinum group metal may be not more than 1, in view of the yield of and selectivity to the desired product.

The reaction of this invention may be carried out in the absence or presence of a solvent which does not inhibit the reaction. As such solvents may be exemplified ethers such as methyl ethyl ether, diethyl ether, dipropyl ether, dimethyl ether, dichloroethyl ether, ethyl phenyl ether, diethylene glycol diethyl ether, triethylene glycol diethyl ether, etc.; esters such as methyl formate, ethyl formate, propyl formate, methyl acetate, ethyl acetate, propyl acetate, and esters of adipic acid, succinic acid, maleic acid, fumaric acid, propionic acid, acetoacetic acid, benzoic acid, etc.; aromatic hydrocarbons such as benzene, nitrobenzene, chlorobenzene, toluene, etc.; alicyclic hydrocarbons such as cyclohexane, etc.

The reaction in this invention may proceed even under extremely mild conditions. The reaction temperature ranges from room temperature to 250° C. preferably from 50° to 150° C. The reaction pressure ranges from atmospheric pressure to 300 atm., preferably from 10 to 200 atm. The ratio by volume of carbon monoxide to unsaturated hydrocarbon (in cases where it is gaseous) ranges from 0.002 to 50, preferably from 0.01 to 5.

In this invention, molecular oxygen may be introduced into the reaction system to increase further the yield and the selectivity of the desired product. As the molecular oxygen may be mentioned oxygen gas, air and other oxygen-containing gases obtained by dilution of oxygen with an inert gas such as nitrogen. Usually, the larger the amount of molecular oxygen introduced, the higher the yield of the desired product. Molecular oxygen should be introduced only to such an extent that the gaseous mixture in the reactor is out of explosion limit, and further it may preferably be introduced in several portions for safety.

EXAMPLE 1

An autoclave made of stainless steel, equipped with a rotary stirrer and having a capacity of 300 ml. was charged with 150 ml. of ethanol, 0.6 g. of palladium-on-activated-carbon (2 wt.%Pd) and 13.3 mg. of palladium chloride $$[\frac{chlorine}{palladium} \text{ (atomic ratio)} = 0.8].$$

After sealing, 27 atm. of ethylene and 18 atm. of carbon monoxide were pressured thereinto. Subsequently, after heating to 90° C., the reaction was carried out for one hour while maintaining the system at the same temperature and supplying 50 ml. of an ethanolic solution containing 20 mmol. of 61 wt.% nitric acid at a rate of 50 ml./hr. During the reaction, each 4 atm. of oxygen was pressured thereinto three times. After completion of the reaction, the reaction mixture was analyzed quantitatively by gas chromatography.

EXAMPLE 2

An experiment was run in the same manner as in Example 1, except that palladium bromide was used in place of palladium chloride in such an amount that the atomic ratio of halogen atoms against palladium atoms might be 0.8.

EXAMPLE 3

An experiment was run in the same manner as in Example 1, except that palladium iodide was used in place of palladium chloride in such an amount that the atomic ratio of halogen atoms against palladium atoms might be 0.8.

EXAMPLES 4 TO 11

Each experiment was run in the same manner as in Example 1, except that 1 g. of palladium-on-activated-carbon (2 wt.%Pd) was used and a halide specified in Table 1 was used in place of palladium chloride in such an amount that the atomic ratio of halogen atoms against palladium atoms might be 0.8.

COMPARATIVE EXAMPLE 1

An experiment was run in the same manner as in Example 1, except that 1 g. of palladium-on-activated-carbon (2 wt.%Pd) was used and palladium chloride was not used.

COMPARATIVE EXAMPLE 2

An experiment was run in the same manner as in Example 1, except that a predetermined amount of palladium nitrate was used in place of palladium chloride.

COMPARATIVE EXAMPLE 3

An experiment was run in the same manner as in Example 1, except that a predetermined amount of palladium sulfate was used in place of palladium chloride.

In each of Examples 1 to 11 and Comparative examples 1 to 3, palladium was used in an amount of 0.188 mmol. in total.

Table 1 shows the results of quantitative analyses by gas chromatography of the reaction mixtures obtained after completion of the reactions.

TABLE 1

| | Halogen compound | | Yield (mmol.) | |
|---|---|---|---|---|
| | Species | Amount used (mg.) | Desired product: diethyl succinate | By-product: diethyl oxalate |
| Example | 1 PdCl$_2$ | 13.3 | 35.4 | 0 |
| | 2 PdBr$_2$ | 20.2 | 40.0 | 0 |
| | 3 PdI$_2$ | 27.4 | 30.4 | 1.4 |
| | 4 LiCl | 6.4 | 34.0 | 0 |
| | 5 ZnCl$_2$ | 11.4 | 26.9 | 4.0 |
| | 6 KCl | 11.2 | 35.1 | trace |
| | 7 NaCl | 8.8 | 37.6 | trace |
| | 8 CoCl$_2$ . 6H$_2$O | 17.9 | 32.9 | 0 |
| | 9 KBr | 18.1 | 45.6 | 0 |
| | 10 KI | 25.1 | 28.5 | 0 |
| | 11 HCl(35 wt. %) | 15.7 | 34.8 | 0.9 |
| Comparative example | 1 not used | | 19.1 | 9.2 |
| | 2 Pd(NO$_3$)$_2$ | 17.3 | 14.1 | 9.0 |
| | 3 PdSO$_4$ . 2H$_2$O | 17.9 | 13.4 | 11.7 |

EXAMPLES 12 TO 14

An autoclave made of stainless steel, equipped with a rotary stirrer and having a capacity of 300 ml. was charged with 100 ml. of methanol, 20 mmol. of 61 wt.% nitric acid, a predetermined amount (specified in Table 2) of palladium-on-activated-carbon (5 wt.%Pd) and a predetermined amount (specified in Table 2) of palladium chloride. After sealing, 33 g. of propylene was pressured thereinto. Subsequently, after carbon monoxide was pressured thereinto to make the total pressure to be 40 atm., the reaction was carried out at 90° C. for one hour. During the reaction, each 4 atm. of oxygen was pressured three times into the reaction system.

Table 2 shows the results of quantitative analyses by gas chromatography of the reaction mixtures obtained after completion of the reactions.

TABLE 2

| | Amount used (mg) | | | Yield (mmol.) | |
|---|---|---|---|---|---|
| Example | Pd-on-activated-carbon | PdCl$_2$ | $\frac{C}{Pd}$ (atomic ratio) | Desired product: dimethyl methyl-succinate | By-product: dimethyl oxalate |
| 12 | 56.7 | 11.9 | 0.22 | 20.5 | 0.4 |
| 13 | 54.0 | 22.5 | 0.40 | 28.2 | 0.9 |
| 14 | 38.0 | 46.6 | 0.85 | 32.0 | 1.3 |

EXAMPLE 15

An autoclave made of stainless steel, equipped with a rotary stirrer and having a capacity of 300 ml. was charged with 50 ml. of isobutanol, 50 ml. of diisobutyl adipate as a solvent, 1 g. of palladium-on-activated-carbon (2 wt.%Pd) and 4 mg. of lithium chloride $$[\frac{chlorine}{palladium} \text{ (atomic ratio)} = 0.5].$$

After sealing and heating the reaction system to 105° C., the reaction was carried out at the same temperature for one hour, passing a gas mixture consisting of 78 vol.% of ethylene, 18 vol.% of carbon monoxide and 4 vol.% of oxygen; maintaining the total pressure at 30 atm.; and supplying isobutyl nitrite continuously at a rate of 39 mmol./hr. After completion of the reaction, the reaction mixture was analyzed quantitatively by gas chromatography. As the result, it was revealed that 20.4 mmol. of diisobutyl succinate was produced and only 1.1 mmol. of diisobutyl oxalate was produced as by-product.

COMPARATIVE EXAMPLE 4

An experiment was run according to the same procedure as in Example 15, except that lithium chloride was not used.

As the result, it was revealed that 12.5 mmol. of diisobutyl succinate was produced and 3.7 mmol. of diisobutyl oxalate was produced as by-product.

EXAMPLE 16

An autoclave made of stainless steel, equipped with a rotary stirrer and having a capacity of 300 ml. was charged with 100 ml. of ethanol, 1.04 g. of palladium-on-activated-carbon (5 wt.%Pd) and 21.6 mg. of palladium chloride $$[\frac{chlorine}{palladium} \text{ (atomic ratio)} = 0.4].$$

After sealing, the reaction system was heated up to 85° C. and the reaction was carried out at the temperature for one hour, passing a gas mixture consisting of 78 vol.% of ethylene, 18 vol.% of carbon monoxide and 4 vol.% of oxygen; maintaining the total pressure at 30 atom.; and supplying 50 ml. of an ethanolic solution containing 20 mmol. of 61 wt.% nitric acid at a rate of 50 ml./hr.

After completion of the reaction, the reaction mixture was analyzed quantitatively by gas chromatography. As the result, it was revealed that 43.2 mmol. of diethyl succinate was produced and only a trace amount of diethyl oxalate was produced as by-product.

EXAMPLE 17

An autoclave made of stainless steel, equipped with a rotary stirrer and having a capacity of 300 ml. was charged with 50 ml. of isobutanol, 1.5 g. of palladium-on-activated-carbon (10 wt.%Pd), 0.03 g. of lithium chloride $$\left[\frac{\text{chlorine}}{\text{pallaium}} \text{(atomic ratio)} = 0.5\right],$$

9.5 g. of isobutyl nitrite and 50 ml. of diisobutyl adipate as a solvent. After sealing, a gas mixture consisting of 86 vol.% of ethylene and 14 vol.% of carbon monoxide was pressured thereinto to make the total pressure to be 50 atm. Subsequently, the contents of the autoclave was heated to 120° C., maintained at the same temperature and the reaction was carried out for 45 minutes until the pressure-drop was not detected any longer.

After completion of the reaction, the reaction mixture was analyzed quantitatively by gas chromatography. As the result, it was found that 18.9 mmol. of diisobutyl succinate was produced and only 2.6 mmol. of diisobutyl oxalate was produced as by-product.

EXAMPLE 18

An autoclave made of stainless steel, equipped with a rotary stirrer and having a capacity of 300 ml. was charged with 50 ml. of isobutanol, 1.5 g. of palladium-on-activated-carbon (10 wt.%Pd), 0.03 g. of lithium chloride $$\left[\frac{\text{chlorine}}{\text{palladium}} \text{(atomic ratio)} = 0.5\right]$$

and 50 ml. of diisobutyl adipate as a solvent. After sealing, a gas mixture consisting of 81.9 vol.% of ethylene, 13.6 vol.% of carbon monoxide and 4.5 vol.% of oxygen was pressured thereinto to make the total pressure to be 20 atm. Subsequently, the contents of the autoclave was heated to 115° C. and maintained at the same temperature, and the reaction was carried out for one hour while supplying the above-mentioned gas mixture at a rate of 0.6 l./min. and nitrogen dioxide gas continuously at a rate of 40 mmol./hr.

After completion of the reaction, the reaction mixture was analyzed quantitatively by gas chromatography. As the result, it was found that 40.6 mmol. of diisobutyl succinate was produced and diisobutyl oxalate was not produced as by-product.

EXAMPLES 19 TO 31

Each chloride specified in Table 3 was added to a distilled water and the resulting mixture was stirred sufficiently.

To an aqueous solution of each chloride was added a predetermined amount of palladium-on-activated-carbon (10 wt.%Pd) and the resulting mixture was stirred for around 30 minutes. Subsequently, after removing the water by distillation at 70° C. with stirring under reduced pressure of 10 to 20 mmHg., the residue was dried at 110° C. for 12 hours to give an activated carbon carrying metallic palladium and the chloride $$\left[10 \text{ wt. \% Pd}, \frac{\text{chlorine}}{\text{palladium}} \text{(atomic ratio)} = 0.5\right].$$

Each experiment was run in the same manner as in Example 15, except that 2 g. of each catalyst thus prepared was used and isobutyl nitrite was supplied at a rate of 70 mmol./hr.

Table 3 shows the chlorides used and the yields of the products.

TABLE 3

| Example | Chloride | Desired product: diisobutyl succinate | By-product: diisobutyl oxalate |
|---|---|---|---|
| | | Yield (mmol.) | |
| 19 | CuCl$_2$ | 94.7 | 1.3 |
| 20 | FeCl$_3$ | 67.3 | 0 |
| 21 | CoCl$_2$ | 56.0 | 2.5 |
| 22 | NiCl$_2$ | 47.5 | 0.2 |
| 23 | ZnCl$_2$ | 54.2 | 0.7 |
| 24 | SnCl$_2$ | 51.3 | 0.7 |
| 25 | SbCl$_3$ | 46.8 | 1.1 |
| 26 | MgCl$_2$ | 68.6 | trace |
| 27 | CaCl$_2$ | 63.0 | 0.7 |
| 28 | MgCl$_2$ | 55.9 | 0.6 |
| 29 | NH$_4$Cl | 51.9 | 1.8 |
| 30 | MnCl$_2$ | 72.3 | 0.8 |
| 31 | NaCl | 35.3 | 1.7 |

EXAMPLES 32 to 34

Each experiment was run in the same manner as in Example 15, except that 2 g. of palladium-on-activated-carbon (10 wt.%Pd) was used as a catalyst and each chloride specified in Table 4 was used in place of lithium chloride in such an amount that the atomic ratio of (chlorine/palladium) might be 0.5.

Table 4 shows the chloride used and the yields of the products.

TABLE 4

| Example | Chloride | Desired product: diisobutyl succinate | By-product: diisobutyl oxalate |
|---|---|---|---|
| | | Yield (mmol.) | |
| 32 | CuCl$_2$ | 66.8 | 0.5 |
| 33 | CaCl$_2$ | 60.5 | 0 |
| 34 | MnCl$_2$ | 64.0 | 0.2 |

EXAMPLE 35

An autoclave made of stainless steel, equipped with a rotary stirrer and having a capacity of 500 ml. was charged with 30 ml. of ethanol, 70 ml. of diethyl adipate as a solvent and 1 g. of the catalyst prepared in Example 19. After sealing, 20 atm. of a gas mixture consisting of 84.8 vol.% of ethylene, 12.0 vol.% of carbon monoxide and 3.2 vol.% of oxygen was pressured thereinto. Subsequently, after the reaction system was heated to 90° C., the reaction was carried out at the same temperature for one hour, while supplying the above-mentioned gas mixture at a rate of 0.56 l./min. and 70 wt.% nitric acid dissolved in a mixed solvent of ethanol and diethyl adipate (3:7, volume ratio) at a rate of 40 mmol./hr. After completion of the reaction, the reaction mixture was analyzed quantitatively by gas chromatography. As the result, it was found that 66.5 mmol. of diethyl succinate was produced and diethyl oxalate was not produced as by-product.

COMPARATIVE EXAMPLE 6

An experiment was run according to the same procedure as in Example 35, except that 1 g. of palladium-on-activated-carbon (10 wt.%Pd) was used as a catalyst. As the results, it was found that 20.1 mmol. of diethyl succinate was produced and 6.7 mmol. of diethyl oxalate was produced as by-product.

EXAMPLE 36

An autoclave made of stainless steel, equipped with a rotary stirrer and having a capacity of 500 ml. was charged with 50 ml. of methanol, 100 ml. of dimethyl adipate as a solvent, 3.91 g. of isobutyl nitrite and 0.2 g. of the catalyst prepared in Example 19, and sealed. Subsequently, 25.4 g. of propylene was pressured thereinto and 10 atm. of carbon monoxide was further pressured thereinto. After heating the reaction system to 95° C. with stirring, 2 atm. of oxygen was pressured thereinto. After the reaction was carried out for around one hour, 2 atm. of oxygen was pressured again thereinto and the reaction was carried out for around one hour. After completion of the reaction, the reaction mixture was analyzed quantitatively by gas chromatography. As the result, it was found that 40.1 mmol. of dimethyl methylsuccinate and 34.8 mmol. of methyl crotonate were produced.

EXAMPLE 37

An autoclave made of stainless steel, equipped with a rotary stirrer and having a capacity of 300 ml. was charged with 50 ml. of isobutanol, 50 ml. of diisobutyl adipate as a solvent and 0.19 mmol. of palladium chloride. After sealing, 20 atm. of a gas mixture consisting of 78 vol.% of ethylene, 18 vol.% of carbon monoxide and 4 vol.% of oxygen was pressured thereinto. Subsequently, after the contents of the autoclave was heated to 105° C. with stirring, the reaction was carried out for one hour while supplying the above-mentioned gas mixture at a rate of 0.6 l./min. and isobutyl nitrite dissolved in a mixed solvent of isobutanol and diisobutyl adipate (1:1, volume ratio) at a rate of 40 mmol./hr. as the result, it was found that 22.5 mmol. of diisobutyl succinate was produced and 0.54 mmol. of diisobutyl oxalate was produced as by-product.

EXAMPLE 38

An experiment was run in the same manner as in Example 37, except that 0.19 mmol. of palladium nitrate and 0.095 mmol. of lithium chloride were used in place of palladium chloride. As the result, it was found 22.7 mmol. of diisobutyl succinate was produced and 0.98 mmol. of diisobutyl oxalate was produced as by-product.

EXAMPLE 39

An experiment was run in the same manner as in Example 37, except that 0.19 mmol. of palladium acetate and 0.095 mmol. of lithium chloride were used in place of palladium chloride. As the result, it was revealed that 20.3 mmol. of diisobutyl succinate was produced and 0.69 mmol. of diisobutyl oxalate was produced as by-product.

COMPARATIVE EXAMPLE 7

An experiment was run in the same manner as in Example 37, except that isobutyl nitrite was not used. As the results, it was found that only 7.8 mmol. of diisobutyl succinate was produced while diisobutyl oxalate was not produced as by-product.

EXAMPLE 40

An autoclave made of stainless steel, equipped with a rotary stirrer and having a capacity of 300 ml. was charged with 60 ml. of methanol, 40 ml. of styrene, 2 g. of palladium-on-activated-carbon (10 wt.%Pd) and 0.11 g. of anhydrous $CuCl_2$ $$[\frac{chlorine}{palladium} \text{ (atomic ratio)} = 0.9].$$

After sealing, 40 atm. of carbon monoxide was pressured thereinto. Subsequently, after heating at 105° C., 50 mmol. of 71 wt.% nitric acid and 4 atm. of oxygen were pressured into the autoclave, and the reaction was carried out for 3 hours at the temperature.

50 mmol. of 71 wt.% nitric acid and 5 atm. of oxygen were added again during the reaction period.

After completion of the reaction, the reaction mixture was analyzed quantitatively by gas chromatography to show that 17.7 mmol. of dimethyl phenylsuccinate was produced.

EXAMPLE 41

An autoclave made of stainless steel, equipped with a rotary stirrer and having a capacity of 300 ml. was charged with 50 ml. of methanol and 50 ml. of cyclohexene, 4 g. of palladium-on-activated-carbon (10 wt.%Pd) and 0.25 g. of anhydrous $CuCl_2$ $$[\frac{chlorine}{palladium} \text{ (atomic ratio)} = 0.9].$$

After sealing, 40 atm. of carbon monoxide was pressured thereinto. Subsequently, the contents of the autoclave was heated to 105° C. and the reaction was carried out for 3 hours after an addition of 50 mmol. of 71 wt.% nitric acid and 5 atm. of oxygen. The same portion of additives were pressured into the reactor one more time in the reaction period.

After completion of the reaction, the reaction mixture was analyzed quantitatively by gas chromatography to show that 28.2 mmol. of dimethyl 1,2-cyclohexane dicarboxylate and 27.2 mmol. of dimethyl 1,3-cyclohexane dicarboxylate were produced.

EXAMPLE 42

An autoclave made of stainless steel, equipped with a rotary stirrer and having a capacity of 300 ml. was charged with 90 ml. of methanol, 10 ml. of dimethyl adipate as a solvent, 2 g. of palladium-on-activated-carbon (10 wt.%Pd) and 0.18 g. of $MnCl_2.4H_2O$ $$[\frac{chlorine}{palladium} \text{ (atomic ratio)} = 0.9].$$

After sealing, 54 g. of isobutene was pressured thereinto and then carbon monoxide was added to make the total pressure to 40 atm. Subsequently, the contents of the reactor was heated to 105° C. and the reaction was carried out for 2 hours after an addition of 50 mmol. of 71 wt.% nitric acid and 5 atm. of oxygen.

After completion of the reaction, the reaction mixture was analyzed quantitatively by gas chromatography to show that 9.2 mmol. of dimethyl 3-methylglutarate was produced.

We claim:

1. A process for preparing a diester of a dicarboxylic acid having two more carbon atoms than the unsaturated hydrocarbon used as the starting material, which consists essentially of reacting in the liquid phase an unsaturated hydrocarbon, carbon monoxide and an alcohol in the presence of a platinum group metal; a compound selected from the group consisting of nitric acid, a nitrogen oxide, and an ester of nitrous acid used in an amount of from 0.0001 to 10 moles per liter of the reaction medium; and a halogen compound selected from the group consisting of (i) a halide of hydrogen, a platinum group metal, an alkali metal, an alkaline earth metal, cobalt, zinc, copper, iron, chromium, antimony, tin and manganese, and (ii) ammonium chloride, said halogen compound being used in an amount such that the ratio of the halogen atoms to the platinum group metal atoms is not more than 1.

2. A process as claimed in claim 1, in which said reaction is carried out in the presence of molecular oxygen.

3. A process as claimed in claim 1, in which said platinum group metal is carried on a carrier.

4. A process as claimed in claim 1, in which said platinum group metal is palladium.

5. A process as claimed in claim 1, in which said nitrogen oxide is nitrogen dioxide.

6. A process as claimed in claim 1, in which said unsaturated hydrocarbon is an aliphatic or alicyclic hydrocarbon having 2 to 20 carbon atoms.

7. A process as claimed in claim 6, in which said unsaturated hydrocarbon is ethylene, propylene, isobutene, styrene, cyclohexene acetylene or an alkyl derivative thereof.

8. A process as claimed in claim 1, in which said platinum group metal is in an amount of from 0.00001 to 10% by weight calculated on the platinum group metal against the reaction medium.

9. A process as claimed in claim 8, in which said platinum group metal is in an amount of from 0.0001 to 1.0% by weight calculated on the platinum group metal against the reaction medium.

10. A process as claimed in claim 1, in which said nitric acid, nitrogen oxide or ester of nitrous acid is used in an amount of from 0.001 to 1 mole per liter of the reaction medium.

11. A process as claimed in claim 1, in which said reaction is carried out at a temperature of between room temperature and 250° C.

12. A process as claimed in claim 11, in which said reaction is carried out at a temperature of between 50° and 150° C.

13. A process as claimed in claim 1, in which said reaction is carried out under a pressure of between atmospheric pressure and 300 atm.

14. A process as claimed in claim 13, in which said reaction is carried out under a pressure of between 10 and 200 atm.

15. A process as claimed in claim 1, in which said carbon monoxide and unsaturated hydrocarbon are used in a molar ratio of from 0.002 to 50.

16. A process as claimed in claim 15, in which said carbon monoxide and unsaturated hydrocarbon are used in a molar ratio of 0.01 to 5.

* * * * *